US006994095B2

(12) United States Patent
Burnett

(10) Patent No.: US 6,994,095 B2
(45) Date of Patent: Feb. 7, 2006

(54) PYLORIC VALVE CORKING DEVICE AND METHOD

(75) Inventor: Daniel R. Burnett, San Francisco, CA (US)

(73) Assignee: Medventure Associates IV, Emeryville, CA (US)

( * ) Notice: Subject to any disclaimer, the term of this patent is extended or adjusted under 35 U.S.C. 154(b) by 0 days.

(21) Appl. No.: 10/671,191

(22) Filed: Sep. 24, 2003

(65) Prior Publication Data

US 2005/0033332 A1    Feb. 10, 2005

Related U.S. Application Data

(60) Provisional application No. 60/490,421, filed on Jul. 28, 2003.

(51) Int. Cl.
*A61B 19/00*    (2006.01)
*A61M 29/00*    (2006.01)

(52) U.S. Cl. ...................... 128/898; 606/192
(58) Field of Classification Search ............... 606/213, 606/192; 128/898; 604/907, 909
See application file for complete search history.

(56) References Cited

U.S. PATENT DOCUMENTS

| | | | | |
|---|---|---|---|---|
| 4,133,315 A | * | 1/1979 | Berman et al. ............ | 606/193 |
| 4,315,509 A | * | 2/1982 | Smit ........................ | 606/108 |
| 4,416,267 A | * | 11/1983 | Garren et al. ............. | 128/898 |
| 4,517,979 A | * | 5/1985 | Pecenka ................... | 606/195 |
| 4,836,204 A | * | 6/1989 | Landymore et al. ....... | 606/215 |
| 5,192,301 A | * | 3/1993 | Kamiya et al. ............ | 606/213 |
| 5,423,872 A | | 6/1995 | Cigaina | |
| 5,634,936 A | * | 6/1997 | Linden et al. ............. | 606/213 |
| 5,782,800 A | * | 7/1998 | Yoon ........................ | 604/514 |
| 5,820,584 A | * | 10/1998 | Crabb ....................... | 604/500 |
| 5,853,422 A | * | 12/1998 | Huebsch et al. ........... | 606/213 |
| 5,976,174 A | * | 11/1999 | Ruiz ......................... | 606/213 |
| 6,102,928 A | * | 8/2000 | Bonutti ..................... | 606/190 |
| 6,112,703 A | * | 9/2000 | Handelsman .............. | 119/707 |
| 6,117,159 A | * | 9/2000 | Huebsch et al. ........... | 606/213 |
| 6,183,520 B1 | | 2/2001 | Pintauro et al. | |
| 6,270,515 B1 | * | 8/2001 | Linden et al. ............. | 606/213 |
| 6,409,656 B1 | | 6/2002 | Sangouard et al. | |
| 6,488,962 B1 | | 12/2002 | Berner et al. | |
| 6,540,789 B1 | * | 4/2003 | Silverman et al. ........ | 623/23.65 |
| 6,544,291 B2 | | 4/2003 | Taylor | |
| 6,558,400 B2 | | 5/2003 | Deem et al. | |
| 6,652,578 B2 | * | 11/2003 | Bailey et al. .............. | 623/1.24 |
| 6,675,809 B2 | * | 1/2004 | Stack et al. ............... | 128/898 |

(Continued)

FOREIGN PATENT DOCUMENTS

WO    WO 02/091961    11/2002

(Continued)

*Primary Examiner*—Gary Jackson
(74) *Attorney, Agent, or Firm*—Townsend and Townsend and Crew LLP

(57) ABSTRACT

Pyloric valve corking devices and methods are described herein. The devices generally include an occluding member which expands from a first configuration to a larger second configuration and a bridging member extending from the occluding member. The bridging member has a length which passes at least partially through the gastric opening such that the occluding member obstructs the gastric opening, and wherein the length permits the occluding member to intermittently move relative to the gastric opening. A second occluding member may be attached to the distal end of the bridging member. The reduction in flow of gastric contents into the duodenum can be tightly regulated using a pump or valve. Otherwise, the flow can be passively regulated with the occluding device.

24 Claims, 15 Drawing Sheets

U.S. PATENT DOCUMENTS

| | | |
|---|---|---|
| 2002/0188354 A1 | 12/2002 | Peghini |
| 2003/0023150 A1 | 1/2003 | Yokoi et al. |
| 2003/0040804 A1 | 2/2003 | Stack et al. |
| 2003/0078611 A1 | 4/2003 | Hashiba et al. |
| 2003/0093117 A1 | 5/2003 | Saadat |
| 2003/0109931 A1 | 6/2003 | Geitz |
| 2003/0109935 A1 | 6/2003 | Geitz |
| 2003/0144708 A1 | 7/2003 | Starkebaum |
| 2003/0153806 A1 | 8/2003 | Miller |
| 2003/0158601 A1 | 8/2003 | Silverman et al. |
| 2004/0172141 A1 * | 9/2004 | Stack et al. ............... 623/23.65 |

FOREIGN PATENT DOCUMENTS

WO    WO 03/017882 A2    3/2003

\* cited by examiner

PYLORIC VALVE CORKING DEVICE AND METHOD

CROSS-REFERENCE TO RELATED APPLICATIONS

This application claims the benefit of priority to U.S. Provisional Patent Application Ser. No. 60/490,421, filed Jul. 28, 2003 and entitled "Pyloric Valve Corking Device and Method" by Daniel R. Burnett), which is incorporated herein by reference in its entirety.

FIELD OF THE INVENTION

The present invention relates generally to weight loss methods and devices. More specifically, the present invention relates to methods and devices for partially and/or intermittently obstructing or reducing the flow of gastric contents across the pyloric valve.

BACKGROUND OF THE INVENTION

Obesity is a condition that is of epidemic proportions in the United States. Recent government studies have indicated that up to 40% of Americans are obese and, of those, almost 20% are morbidly obese. In and of itself, though, obesity is not the problem. The difficulty with obesity arises with the multiple conditions, including cardiovascular disease, diabetes, and obstructive sleep apnea, that occur with this ubiquitous problem. There have been many attempts among the prior art to treat obesity, all of which either have serious side effects or are ineffective.

For example, various diets, supplements and pharmaceuticals have been developed and marketed in an attempt to treat obesity. None of these, though, have had any significant benefit to date with the exception of some of the pharmaceuticals which have also been associated with many serious, life-threatening conditions. To date, there are no commercially available supplements or drugs on the market that have been found to have significant success in weight reduction.

Recognizing this, the medical industry has begun turning to more extreme measures, the best example of which is the Roux-En-Y gastric bypass. More effective, but also potentially lethal, this major surgery with 1–2% mortality, 6 month recovery period and a price tag of tens of thousands of dollars, is still increasing in popularity due to the inefficacy of other treatments. Gastric reduction, or simply removing a large segment of the stomach, is similar to gastric bypass in its potentially lethal complications.

There is evidence, though, that benefit can be derived from the reduction in gastroduodenal flow. For instance, as presented at the American Society for Bariatric Surgery conference in June 2003, it has been discussed that stimulation of the gastric vagus nerve with subsequent reduction in gastric motility resulted in loss of over 20% of excess weight in a nine month period. Furthermore, there is data suggesting that a gastric vagotomy is also effective in the treatment of obesity trough a similar mechanism. These therapies, though, require highly invasive, sometimes irreversible, surgical procedures.

SUMMARY OF THE INVENTION

The current invention, on the other hand, is completely non-invasive and completely reversible. Thus, in the treatment of obesity and other conditions in which delayed gastrointestinal transit is desirable, the devices described herein allow for the safe, controlled reduction of gastroduodenal flow in a completely reversible manner. The devices generally comprise an occluding member adapted to expand from a first configuration to a larger second configuration and a bridging member extending from the occluding member, the bridging member having a length which is adapted to pass at least partially through the gastric opening such that the occluding member obstructs the gastric opening, wherein the length is further adapted to permit the occluding member to intermittently move relative to the gastric opening. More particularly, a system incorporating the devices described herein may comprise a first occluding member and a second occluding member each adapted to expand from a first configuration to a larger second configuration, a bridging member extending between the first and the second occluding members, wherein the bridging member has a length which is adapted to pass through the gastric opening such that the first occluding member obstructs the gastric opening and is retained by the second occluding member, and wherein the bridging member is further adapted to permit the first occluding member to intermittently move relative to the gastric opening.

The device may be configured to decrease the flow of contents from the gastric space, e.g., the stomach, into the intestinal tract. This may be accomplished generally through the placement of a transpyloric device which is easily placed and removed. Once placed, the device may partially and/or intermittently obstruct the pylorus, thereby decreasing the flow of gastric contents into the duodenum.

The reduction in flow through the pylorus can be tightly regulated with an active device, e.g., a pump or metering valve, which, in the case of a pump, may be designed to pump the contents of the stomach into the intestine or, in the case of a metering valve, may be designed to actively control the flow therethrough. Either the pump and/or the metering valve can be operated and powered externally. This active valve or pump variation may also incorporate temperature, pressure, or pH sensors in order to determine when the active valve or pump should be engaged. Moreover, this reduction in flow can be more loosely regulated through the use of a passive flow reduction mechanism which spans the pyloric valve and decreases the effective diameter of the pyloric valve. Furthermore, both the active and passive embodiments can be adapted to incorporate slow-release drug delivery and electrical stimulation technologies.

Applications for such an invention include weight reduction and treatment of malabsorption syndromes, among others. In addition to the reduction of gastroduodenal transit, the active mechanisms can be used to increase transit, thereby causing the dumping characteristic of an effective gastric bypass surgery. Both of the variations, as well, can incorporate an expansile foam in the inflatable portion in order to prevent accidental rupture of the device with subsequent intestinal migration. With the presence of foam, any potential puncture of the inflatable membrane (ideally made of silicone or other biocompatible material) would result in maintenance of volume of the present invention.

The devices can be placed either using endoscopy with direct placement, or through simple ingestion with programmed inflation of the occlusion members to effect the pyloric anchoring. For example, one of the occlusion members could have its inflation port covered by an acid-sensitive coating while the other is acid-resistant but erodes at the pH found in the intestine (~6.0). Thus, once the device is ingested, one of the occlusion members will expand retaining the device in the gastric space after which gastric motility will eventually move the remaining uninflated occlusion member into the intestine. Once the second, occlusion member contacts the intestinal tract, the inflation port may be eroded by the intestinal milieu and the second portion may slowly inflate leaving the device spanning the pyloric valve.

During removal, the device may be equipped with a metallic ring around its inflation port in the gastric space. Once removal is desired, a magnet-tipped suction catheter may be advanced into the patient (or placed using a nasogastric tube). Once an optional sensor has indicated that the magnet has engaged the metallic ring, a vacuum may be activated and the entire device deflated through rupture of a pressure-sensitive barrier in the case of the dual inflation mechanism, or through simple application of vacuum forces. In the dual inflation port variation, while the intestinal port may remain open, the inflation port may be designed for low-flow such that a vacuum force will overwhelm its intake capabilities and allow for the decompression of the entire device. In the instance that the device has been ruptured or punctured and suction is not able to compress the expansile foam, the device may be removed using endoscopy.

In alternative variations, the device can be composed of a slowly degrading polymer placed either through endoscopy or through ingestion. In yet another variation, the device can be placed by endoscopy and be formed from semi-rigid compounds to ensure its integrity in the hostile gastric environment. The inflatable portion of the device could take virtually any shape provided that it intermittently occludes the pyloric valve and does not cause permanent occlusion. The bridging member between the inflatable portions can be a variety of sizes including a millimeter or less (in order to not significantly reduce pyloric sphincter diameter) up to 8–10 mm (to severely reduce the functional diameter of the pyloric sphincter and achieve obstruction of flow in this manner as well).

The devices may also be utilized with a number of gastric fillers. The devices may be used to prevent premature passage of the gastric filler as well as to maintain a sensation of fullness for the patient. To this end, the bridging member or tether between the two occlusion members can be of varying diameter ranging from less than 1 mm up to 10 mm in diameter to provide reduction of the functional diameter of the pyloric sphincter and/or to prevent premature intestinal migration of a gastric filler. The gastric filler used with this device may be as simple as a dietary fiber to as complex as a specifically designed polymer. Regardless of the filler used, the devices may assist in gastric retention of the filler.

The devices described herein may incorporate a number of safety features. For instance, the devices may incorporate an expansile foam inside the expanding portions of the device. This expansile foam may ensure that any minimal (or even extensive) puncture will not result in distal migration of the device with potential small bowel obstruction. Instead, the device will remain in place straddling the pylorus leaving the remainder of the bowel undisturbed. The external surface of the device may be made of a variety of biocompatible materials, e.g., silicone, although any biocompatible, airtight surface will do Another safeguard may include the use of bright coloring in the expansile foam, e.g., visually distinct dyes or markers. Thus, with instructions to examine their feces (at least cursorily), the patients or physicians will have an indication that there may be compromise of the device, however unlikely, if there are brightly colored flecks in their feces. Alternatively, the device may be designed to compress with rupture. In this variation, the device may omit any expansile foam, but instead have an inherent elasticity which provides for complete collapse of the device with rupture. This collapsibility could be provided by elastic members inside the inflatable members or use of an elastic material for the device itself. This safeguard may not prevent intestinal passage, but may instead encourage complete passage through the entire bowel in the instance of rupture.

DETAILED DESCRIPTION OF THE INVENTION

Figure 1A:
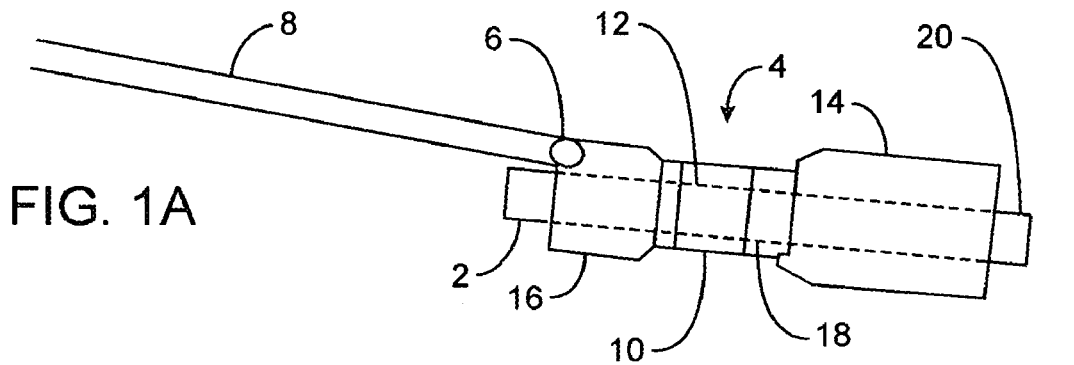
FIGS. 1A to 1C show cross-sectional views of one variation of a pyloric corking device designed to partially and/or intermittently obstruct a gastric opening in an unexpanded, partially unexpanded, and fully expanded configuration, respectively.
Figure 1B:
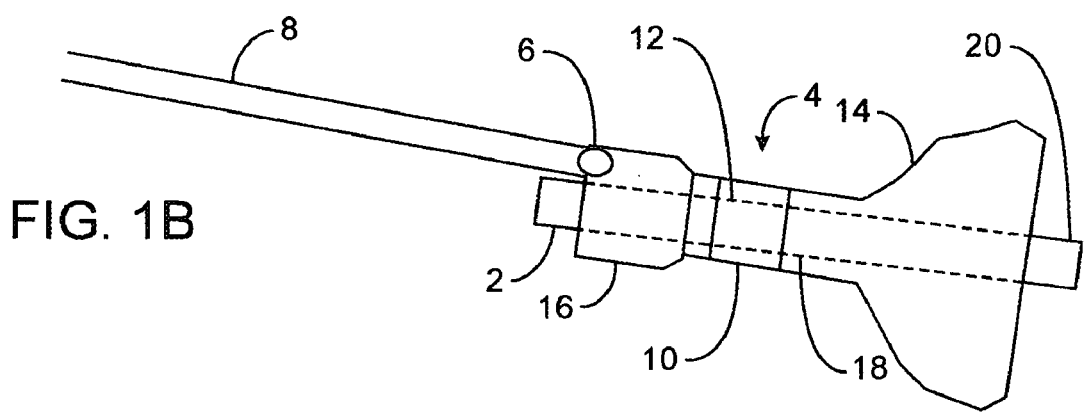
Figure 1C:
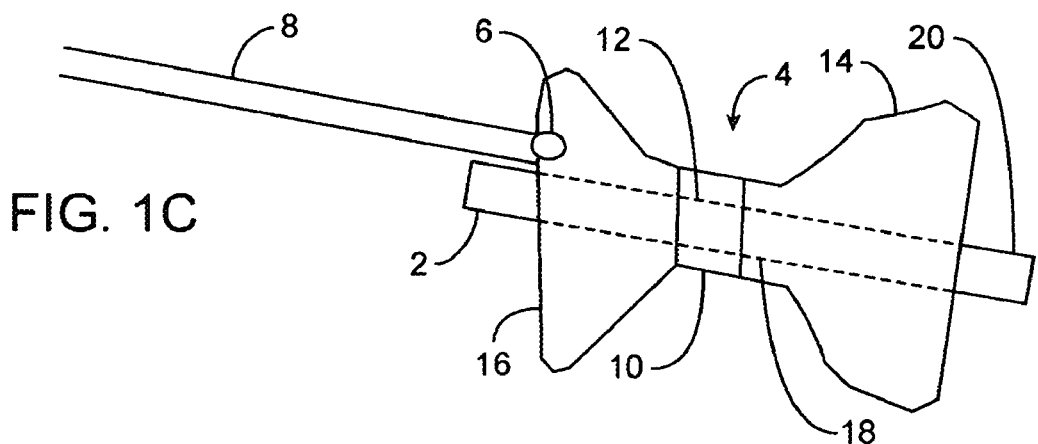

FIGS. 1A to 1C are cross-sectional views showing the expansion, respectively, of one variation of a pyloric corking device which is designed to partially and/or intermittently obstruct a gastric opening, particularly the pyloric valve. In this particular variation, FIG. 1A illustrates the device 4 in an unexpanded or uninflated state and ready for delivery and/or insertion into the pyloric valve. FIG. 1B shows the distal occlusion member 14 in an expanded state. In use, once the device 4 has been placed, e.g., in the pyloric region or beyond, the distal occlusion member 14 may be inflated through the influx of any number of biocompatible fluids or gases, e.g., saline, water, air, nitrogen, etc., through the tubing 8 leading to the inflation port 6, which may be self-sealing. Tubing 8 may include any number of delivery tubes such as catheters, endoscopes, etc.

The distal occlusion member 14 may be configured to inflate before the inflation of proximal occlusion member 16 by fabricating the inflatable member of distal occlusion member 14 with a material which is more easily distensible relative to a material of the proximal occlusion member 16. Materials which may be used in fabricating the occlusion members 14, 16 may include any number of materials such as silicone, silicone elastomers, latex, polyurethane, PTFE, FEP, etc. Alternatively, self-expanding materials, such as foam or hydrogels which typically expand upon contact with fluids, may be utilized within the occlusion members 14, 16. If such self-expanding materials are utilized, they may be disposed in the occlusion member 14, 16 and a fluid such as saline, may be infused to expand the materials. Different self-expanding materials may be incorporated in the distal occlusion member 14 than in the proximal occlusion member 16 to obtain differing radial pressures exerted by the expanding materials.

In yet another alternative, an expanding scaffolding may be utilized within each of the occlusion members 14, 16. Such a scaffold may be made of a shape memory alloy or super-elastic alloy, such as Nitinol. The scaffold may be compressed into a delivery configuration and then either allowed to expand into the desired occlusive shape by self-expansion or by supplying an activation energy, e.g., electrical, heat, RF energy, etc. In either case, the distal occlusive member 14 may be positioned distal of the pyloric valve and then inflated or expanded into its larger configuration. It may then be pulled proximally against the pyloric annulus, at which point proximal occlusive member 16 may be inflated or expanded by infusion through port 6, as shown in FIG. 1C. With both occlusion members 14, 16 inflated or expanded, bridging member 10 connecting the two may span the pylorus. Bridging member 10 may be of various diameters, e.g., 1 mm and less (in order to not significantly reduce pyloric sphincter diameter) or up to 8–10 mm in diameter (to severely reduce the functional diameter of the pyloric sphincter and achieve obstruction of flow in this manner as well).

Bridging member 10 may be designed to have a flexible length sufficient to allow the occlusion members 14, 16 to maintain its position with respect to the pyloric valve yet still enable the members 14, 16 to move. Proximal occlusion member 16 may move from fully obstructing the pyloric valve to moving proximally of the pyloric valve to the extent that distal occlusion member 14 allows member 16 to move. This movement may be elicited by the natural movements of the gastric lumen (stomach) and muscles surrounding the pyloric valve. Thus, when proximal occlusion member 16 is moved proximally, the pyloric valve is only partially obstructed and may allow for the intermittent passage of food-between the bridging member 10 and the valve. Because any food within the stomach is retained for longer periods of time, feelings of satiation may be initiated sooner and prolonged so that the patient consumes less food. Moreover, to allow for the relative movement of the occlusion members 14, 16, bridging member 10 may be of a length which is sufficient to allow for its placement through the pyloric valve (or through another gastric opening) such that there is sufficient tolerance for the occlusion members 14, 16 to move proximally and distally relative to the pyloric valve. For instance, in the event that a patient's pyloric valve extends about 2 cm in length, the bridging member 10 is preferably longer than 2 cm, for example, up to 5 cm in length. Moreover, while occlusion members 14, 16 are inflatable or expandable, bridging member 10 itself may be configured to inflate or expand in diameter.

A visible dye or marker, preferably being highly visible, may optionally be infused into one or both of the occlusion members 14, 16 to function as a safety measure. Alternatively, one or both of the occlusion members 14, 16 may optionally be fabricated from a material which is highly visible and visually distinct from tissue so that in the unlikely event of an occlusion member 14, 16 rupturing, the dye or pieces of the occlusion member 14, 16 may become visible once passed from the body. This may indicate to the patient or physician that a rupture of the device has occurred.

Another variation may incorporate slow-releasing drugs infused into the materials covering the device or materials incorporated into the device. These drugs, which may be any number of drugs, may slowly infuse into the patient by drug release into the intestinal tract or through contact with the patient. Alternatively, the devices may incorporate electrical stimulation technologies. For instance, electrical probes may extend from a surface of the device for insertion into the surrounding tissue or electrodes may be formed over a surface of the device instead.

In yet another alternative, the occlusion members 14, 16 may be covered by an erodable or biodegradable covering over one or both members 14, 16. Such a covering may be configured to constrain one or both members 14, 16 and once the device has been ingested or placed within the gastric lumen, contact with the surrounding fluids may naturally erode the covering thus allowing the covered occlusion member to expand or inflate. In another variation, proximal and distal occlusion members may each be covered by different materials each configured to erode at differing rates or in different environments, as described in further detail below.

In the variation shown in FIGS. 1A to 1C, the device 4 may include an optional lumen 18 defined through the device 4. Optional lumen 18 may allow for the passage of fluids and food through the device 4 entering the lumen 18 through entry port 2 and exiting through the exit port 20. The lumen 18 may be designed to allow for the passage of a reduced volume of food through the device 4, in which case the device 4 shown may be configured with a relatively shortened bridging member 10 to inhibit the relative movement of the device 4 relative to the pylorus. With this variation, the lumen 18 has been configured so that it may be capable of actively pumping or metering the contents of the gastric lumen 74 into the intestine 76 through the device 4. In such a case, the need for the device 4 to be able to move to un-occlude the pyloric valve is removed. As shown in the figures, an optional pump or active metering valve 12 may be incorporated into the device 4. Pump or valve 12 may be configured to simply open and allow for the passage of the stomach contents through lumen 18 and valve 12 upon sensing the presence of foreign objects, such as food, in the stomach or upon sensing a predetermined pressure from the contents. Other sensing parameters may include temperature and pH levels. Alternatively, the pump or valve 12 may be configured to actively pump the stomach contents through the lumen 18 via a pumping mechanism automatically activated by pump or valve 12 or externally activated by the patient or physician through wireless communication. In the case where the device is configured with a valve 12, the valve may be configured as a unidirectional valve to allow the flow of fluids and food only from the stomach to the intestinal tract.

Figure 2A:
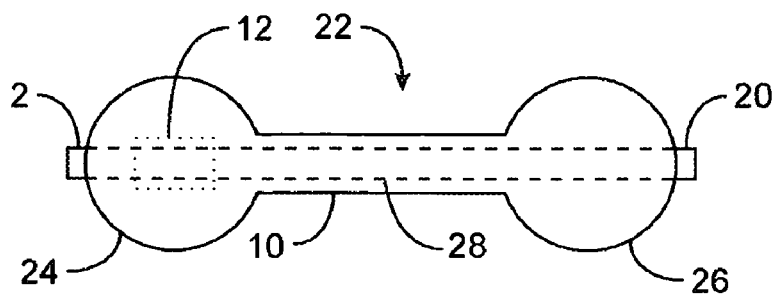
FIGS. 2A to 2D show side views of variations of the device utilizing occlusion members of different shapes.

The device 4 could have any shape provided that the shape and/or total volume of the proximal occlusion member 16 is sufficient to prevent its passage through the pyloric valve and into the intestines. FIGS. 2A to 2D show side views of different shape variations which are possible for use as occlusion members. For instance, FIG. 2A shows a side view of a device variation 22 in which proximal and distal occlusion members 24, 26 have a cross-sectional shape along a longitudinal axis defined by the device 22 in the form of circles, to form spherical occlusion members. Although proximal and distal occlusion members 24, 26 are illustrated having equally sized diameters, the diameters may be varied depending upon the desired shape and device configuration. For instance, proximal occlusion member 24 may be configured to have a diameter larger than distal occlusion member 26. Alternatively, a device having the opposite configuration may also be utilized, although this may be less preferable. Lumen 28 and pump or valve 12 may be optionally included, again depending upon the desired device configuration.

Figure 2B:
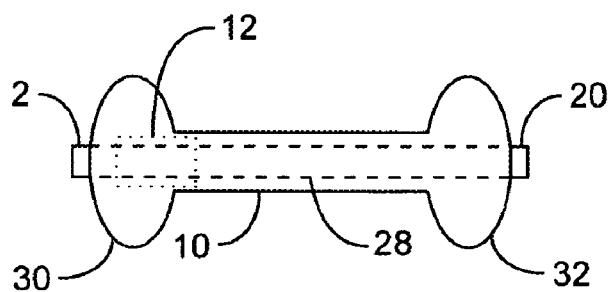
Figure 2C:
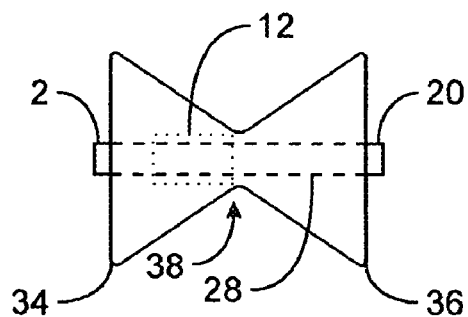
Figure 2D:
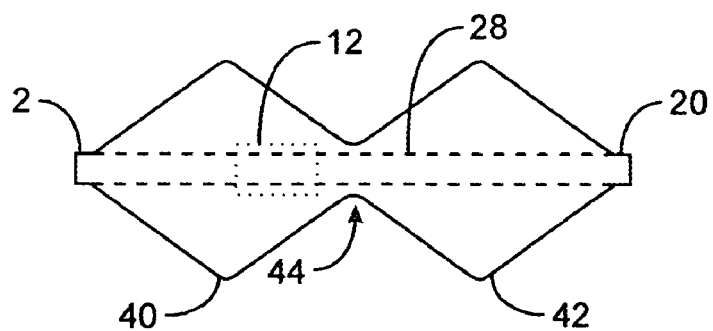

FIG. 2B shows another device variation in which proximal and distal occlusion members 30, 32 may have a cross-sectional shape along a longitudinal axis defined by the device in the form of ellipses, to form ellipsoids. The major axes of the elliptically-shaped occlusion members 30, 32 is preferably oriented perpendicularly relative to the longitudinal axis of the device in this variation, although various angles may be formed as well. FIG. 2C shows the variation in which proximal and distal occlusion members 34, 36 may be formed as triangles, to form conically-shaped occlusion members. In this variation, bridging member 38 may be minimal in length and may simply be formed by the intersection of the occlusion members 34, 38 to form a waist region. FIG. 2D shows yet another variation in which proximal and distal occlusion members 40, 42 may be formed as diamond shapes, to form a variation of conically-shaped occlusion members. This variation may also form a waist region 44.

Although these variations show specific shapes, these are merely intended to be illustrative of the various types of shapes which may be utilized and is not intended to be limiting. For instance, any shape, such as rectangles, squares, etc., which may function to occlude a gastric opening and prevent the device from falling therethrough may be utilized and are within the scope of this disclosure. Moreover, various combinations of the different shapes as occlusion members on a single device may also be utilized, such as a device having a distal occlusion member in the shape of a sphere and a proximal occlusion member in the shape of a cone.

Figure 3A:
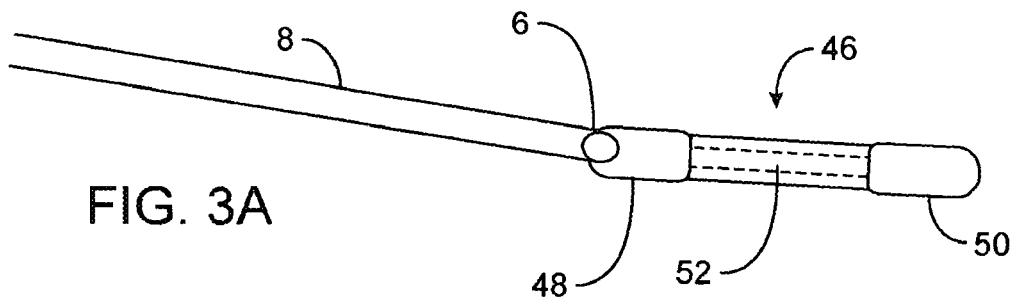
FIGS. 3A to 3C show cross-sectional views of another variation of the pyloric corking device.
Figure 3B:
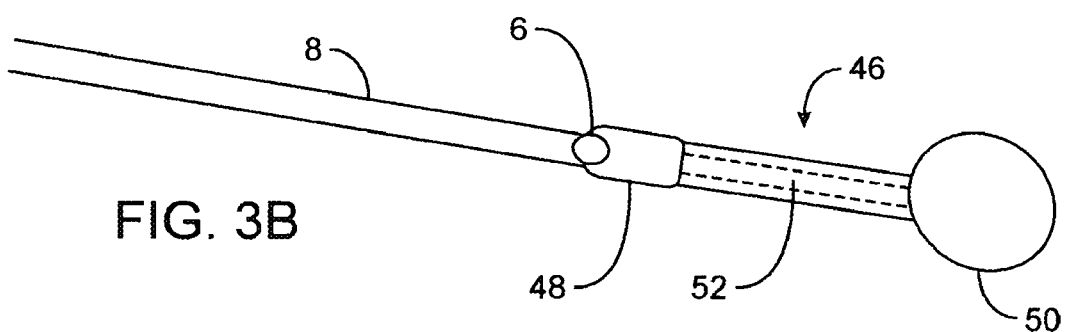
Figure 3C:
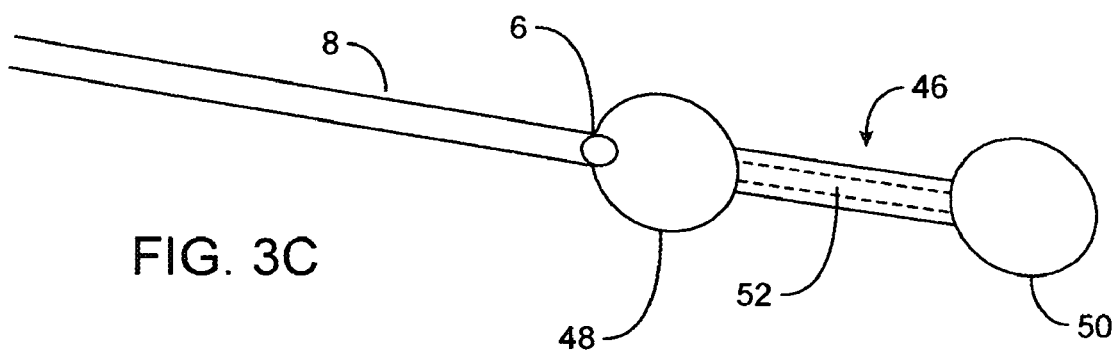

FIGS. 3A to 3C show cross-sectional views of another variation of a pyloric corking device which is also designed to intermittently obstruct a gastric opening. Similar to the device shown in FIGS. 1A to 1C, this particular variation omits the use of a lumen defined through the entire device 46. This device 46 may also incorporate any of the features described above for expanding the occlusion members. For instance, foam of varying expansion pressures may be utilized to ensure that expansion occurs in the distal occlusion member 50 prior to expansion in the proximal occlusion member 48 upon the injection of a fluid, e.g., saline or water, into the device 46. The device 46 has been designed though, so that the influx of fluids from the infusion tubing 8 through the entry port 6 is channeled through the lumen 52 of the central portion from the proximal occlusion member 48 to the distal occlusion member 50. The device 46 may also be placed in the same manner as the device of FIGS. 1A to 1C, as described in further detail below. This variation may also incorporate an inflation port 6, which may be metallic, so that removal of the device 46, if necessary, can be accomplished through the simple placement of a magnetically tipped suction catheter. The catheter, when appropriately placed, may cause the device to deflate by applying a suction force to facilitate the easy removal of the device 46 from the pyloric valve. The device 46 can thus be removed through any endoscopic or percutaneous approach, e.g., an oro- or naso-gastric approach. While this variation may have a lumen 52 connecting the proximal 48 and distal 50 occlusion members, this lumen 52 may be closed to gastric space and instead be used to communicate an inflation fluid to inflate the occlusion members 48, 50. The occlusion members of the device 46 may have any shape as described above, for instance in FIGS. 1A to 2D.

Figure 4A:
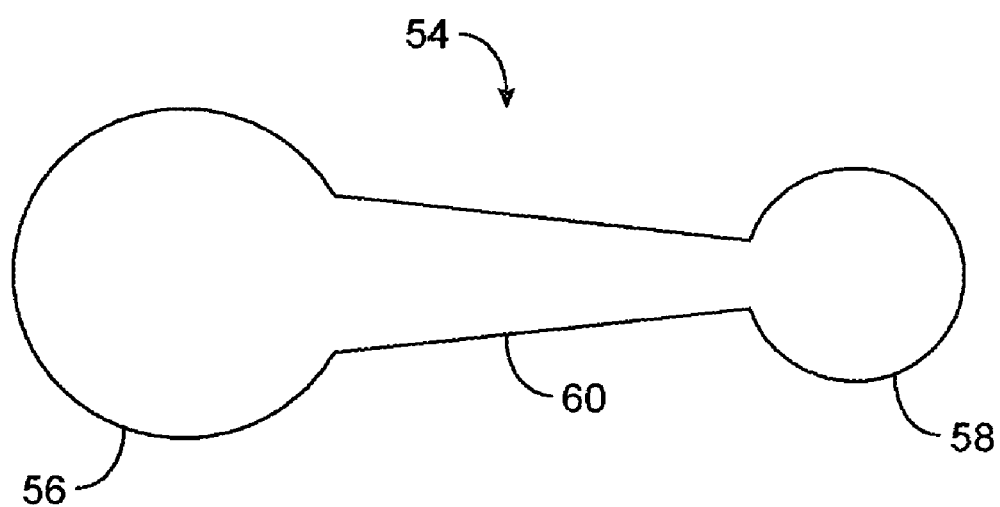
FIG. 4A shows a side view of yet another variation of the device having a tapered bridging member.

Yet another variation of the device is shown in FIG. 4A. In this variation the device 54 may have a bridging member 60 which is tapered. The bridging member 60 may be tapered to become wider along its length from the distal occlusion member 58 to the proximal occlusion member 56. The tapered bridging member 60 may be utilized to facilitate movement of the device 54 to un-occlude the pyloric valve. As the pyloric valve contracts about the bridging member 60, the taper may aid in moving the device proximally. The angle of the taper may be varied, depending upon the desired results, as may the size and shapes of the occluding members 56, 58.

Figure 4B:
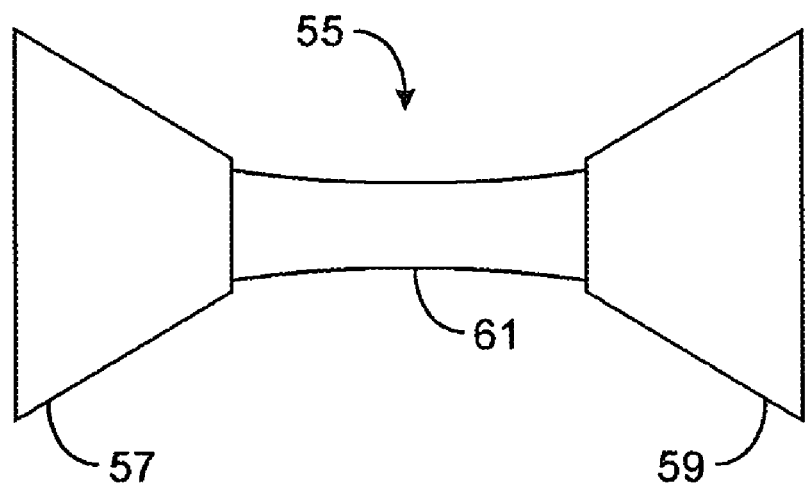
FIG. 4B shows a side view of yet another variation of the device having conical occlusion members held at a distance from one another.

FIG. 4B shows yet another variation similar to that shown above. In this variation, the device 55 may have occlusion members 57, 59 having conically-shaped members which are connected via a bridging member 61. This bridging member 61 may have a length which holds occlusion members 57, 59 at a distance from one another sufficient to enable the device 55 to move relative to the pyloric valve. The device 55 may inflate or expand the occlusion members 57, 59 using any of the methods disclosed herein and the device 55 may also optionally incorporate a central lumen and a passive or active valve or pumping mechanism, if desired.

In yet another variation, the distal occlusion member may be omitted entirely.

Figure 5A:
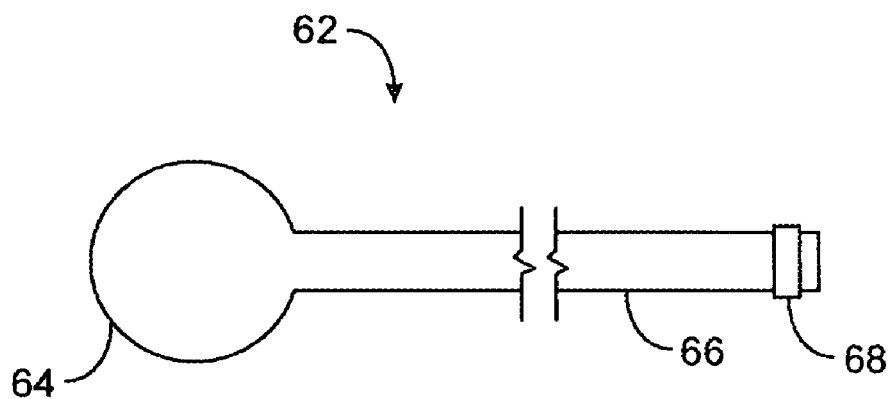
FIGS. 5A and 5B show side views of yet another variation of the device having a single occlusion member and alternative anchor members.
Figure 5B:
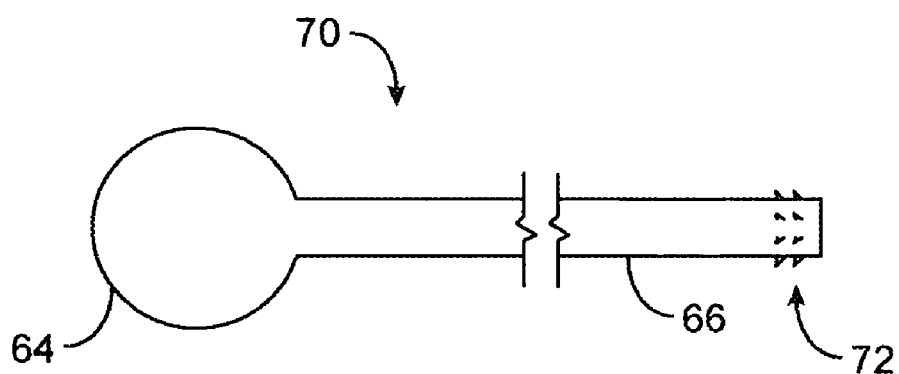

FIG. 5A, for instance, shows a side view of an alternative variation 62 in which the bridging member 66 may extend at some length, e.g., 5 cm or greater, from a proximal occlusion member 64. The bridging member 66 may be placed within the intestinal tract, e.g., the duodenum, while held in place by the proximal occlusion member 64 abutting the pyloric valve. The positioning of the proximal occlusion member 64 relative to the pyloric valve may be maintained by the frictional forces generated by the bridging member 66 rubbing against the walls the intestinal tract. The occlusion member 64 may function in the same manner as described above in intermittently un-occluding the pyloric valve during stomach contractions and movement, but may be held in place by the length of the bridging member 66. Although the distal end of the bridging member 68 may be free-floating in the intestinal tract, it may optionally be weighted by a weight 68 or by a number of hooks or barbs 72 for attachment to the intestinal walls, as shown in the device 70 of FIG. 5B.

It is furthermore within the scope of this disclosure that certain features between the different device variations described herein may be incorporated into various combinations. For instance, a device having a proximal occlusion member having a spherical shape and a distal occlusion member having a conical shape may be utilized. As a further example, this device may also incorporate various methods to inflate or expand the distal occlusion member in a different manner as the proximal occlusion member. Moreover, this device may also have a biodegradable covering over only one occlusion member and may also incorporate the valve and/or pump integrated within the device and may also optionally include a lumen defined throughout the length of the device. These examples are merely intended to be illustrative of the various combinations which may be employed by combining various aspects from different variations described herein and are intended to be within the scope of this invention.

Figure 6A:
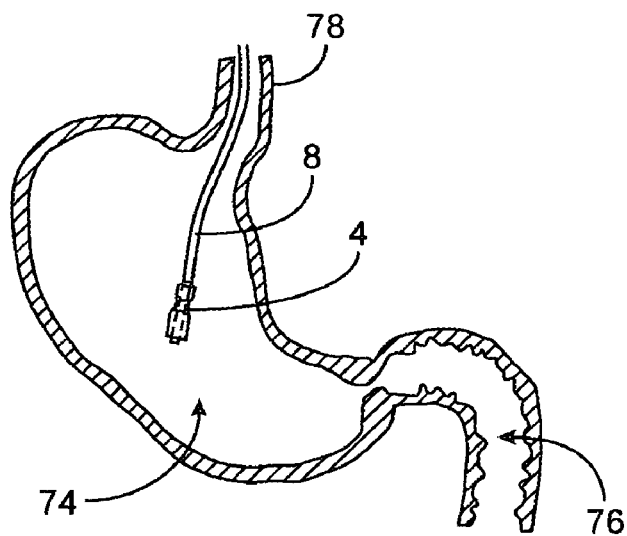
FIGS. 6A to 6C show cross-sectional views of the stomach and one variation for nasogastric (or endoscopic) placement of a non-ingestible variation of the device.
Figure 6B:
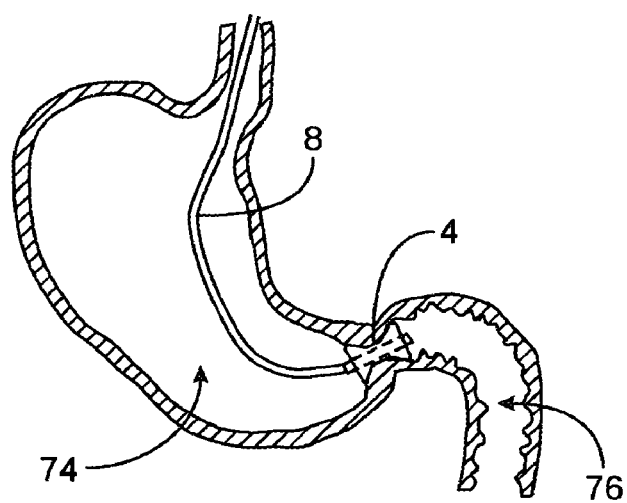
Figure 6C:
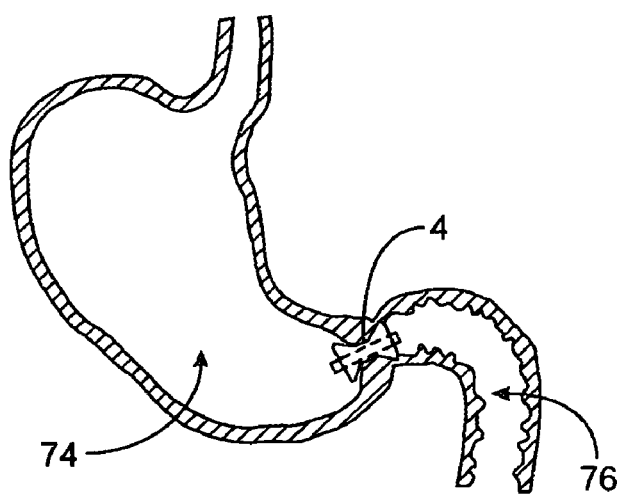

FIGS. 6A to 6C show cross-sectional views of the stomach and one variation for nasogastric (or endoscopic) placement of a non-ingestible, active variation of the device 4. As the device 4 is delivered through the esophagus 78, it may be in a compressed, un-inflated, or un-expanded configuration, as shown in FIG. 6A, while being positioned via the optional tubing 8. Once the device 4 has been positioned to span the pylorus with the occlusion members in the stomach 74 and duodenum 76, respectively, the device 4 may be inflated or expanded using any of the methods described above, as shown in FIG. 6B. The tubing 8 may then be detached and the device 4 left in place, as shown in FIG. 6C.

Figure 7A:
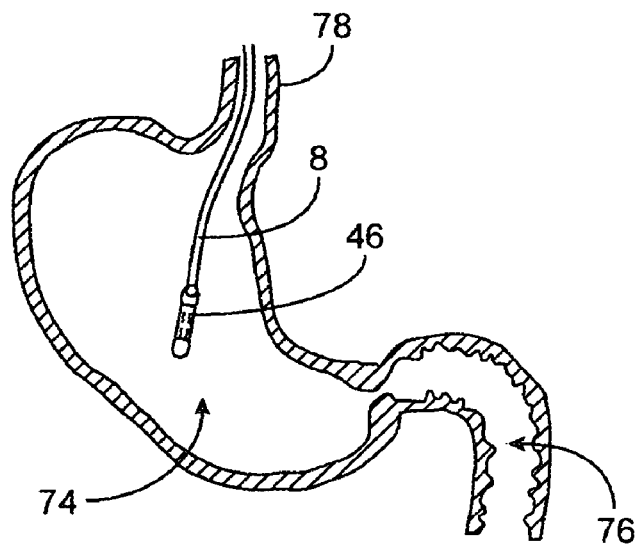
FIGS. 7A to 7C show cross-sectional views of the stomach and another variation for nasogastric (or endoscopic) placement of a non-ingestible variation of the device.
Figure 7B:
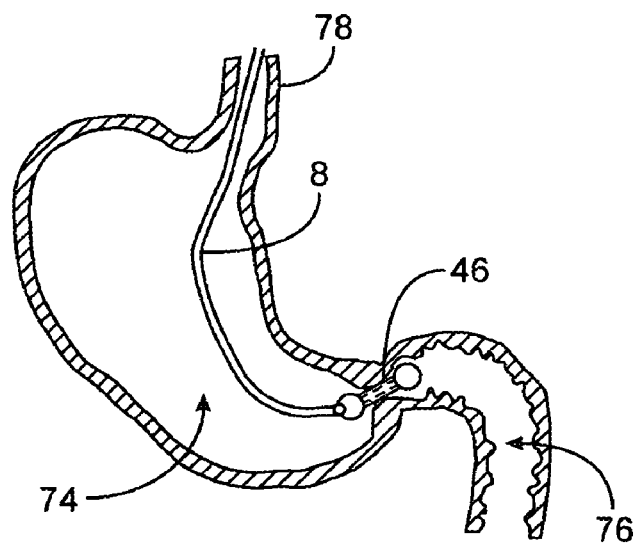
Figure 7C:
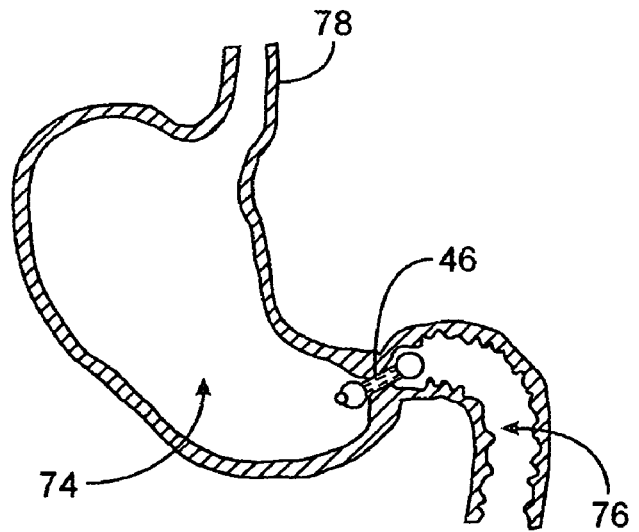

FIGS. 7A to 7C show cross-sectional views of the stomach and another variation for nasogastric (or endoscopic) placement of a non-ingestible, passive variation of the device 46. As above, the device 46 may be advanced through the esophagus 78 while in a compressed, un-inflated, or un-expanded configuration, as shown in FIG. 7A. As shown in FIG. 7B, once the device 46 has been placed spanning the pylorus with the occlusion members in the stomach 74 and duodenum 76, respectively, the device may be inflated or expanded and the tubing 8 may be detached and the device 46 left in place, as shown in FIG. 7C.

Figure 8A:
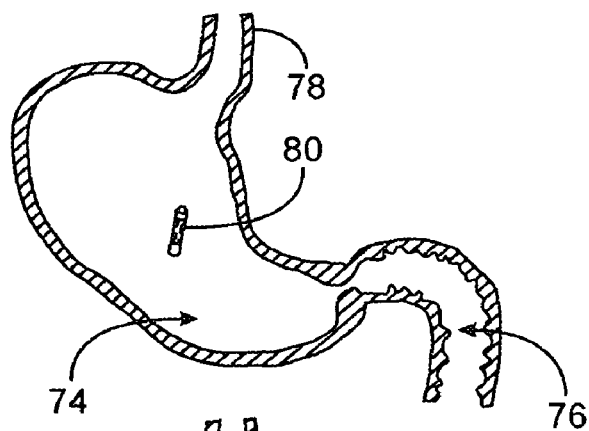
FIGS. 8A to 8D show cross-sectional views of the stomach and yet another variation for placement of a variation of the device through ingestion.
Figure 8B:
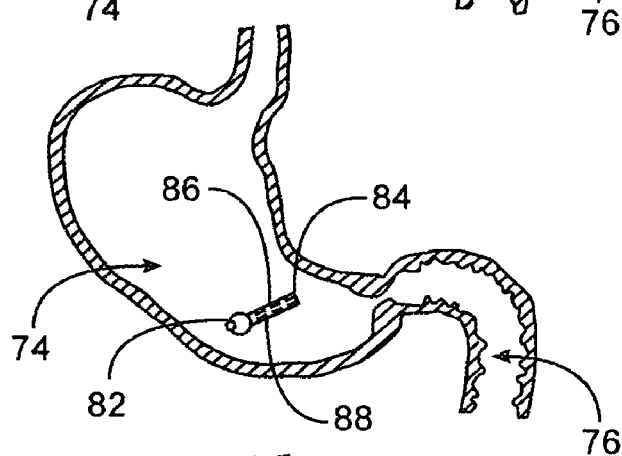
Figure 8C:
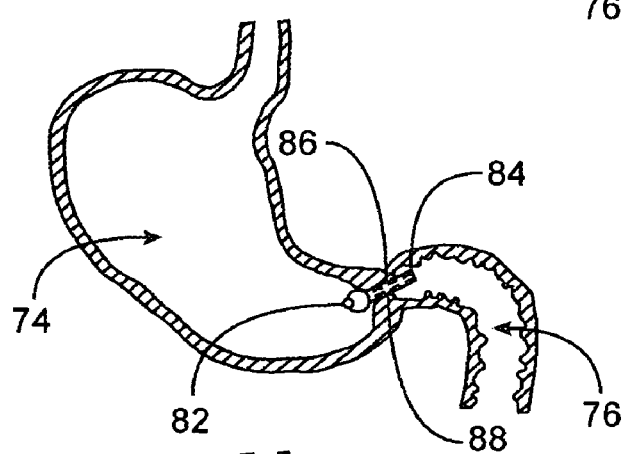
Figure 8D:
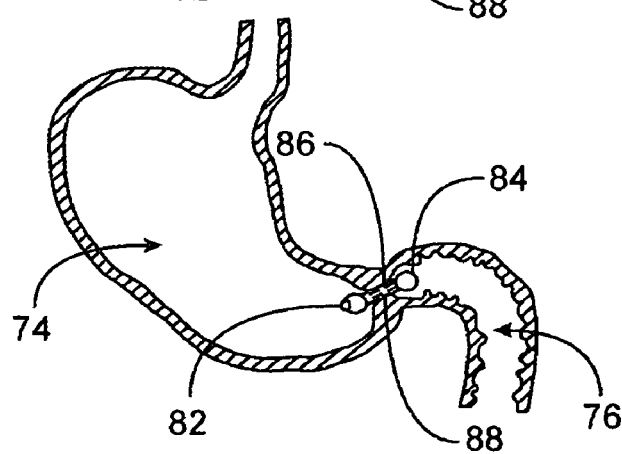

FIGS. 8A to 8D show cross-sectional views of the stomach and yet another variation for placement of a passive embodiment of the device 80. As shown in FIG. 8A, the device 80 may be simply ingested. As it enters the stomach 74, gastric fluids may erode an acid sensitive coating over the inflation port of the proximal occlusion member 82. Once the coating has degraded, the proximal occlusion member 82 may be configured to expand or inflate, as shown in FIG. 8B. Once the expansion or inflation has occurred, the device 80 will remain in the stomach 74 and eventually the distal occlusion member 84 may pass into the duodenum 76 while still in its un-expanded or un-inflated state due to the natural contractions of the stomach, as shown in FIG. 8C. Once the distal occlusion member 84 has passed into the duodenum 76, an alkaline sensitive coating over the distal occlusion member 84 may be eroded and expansion or inflation of the distal occlusion member 84 will occur with the device spanning the pyloric valve, as shown in FIG. 8D. The covering over the distal occlusion member 84 may be configured to erode only once it has contacted the acidic environment specific to the duodenum 76, where the pH level is approximately 6. In order to facilitate removal, the two occlusion members 82, 84 may be connected by a central, hollow lumen 86, as described above, with a barrier 88 designed to rupture upon the application of a predetermined pressure level. Thus, with application of a vacuum having the appropriate pressure level, the barrier 88 may be configured to rupture and the entire device 80 may be deflated.

Figure 9A:
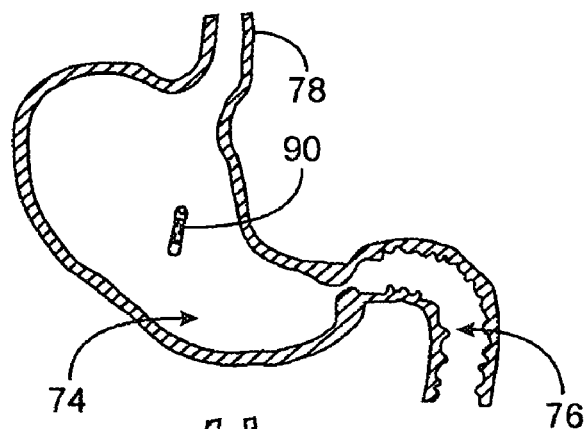
FIGS. 9A to 9D show cross-sectional views of the stomach and yet another variation for placement of another variation of the device through ingestion.
Figure 9B:
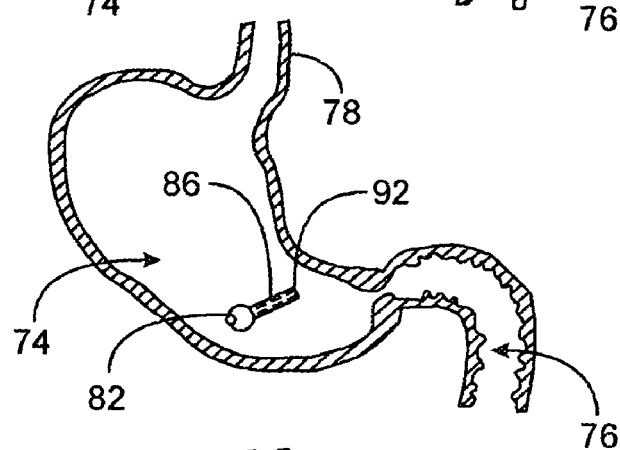
Figure 9C:
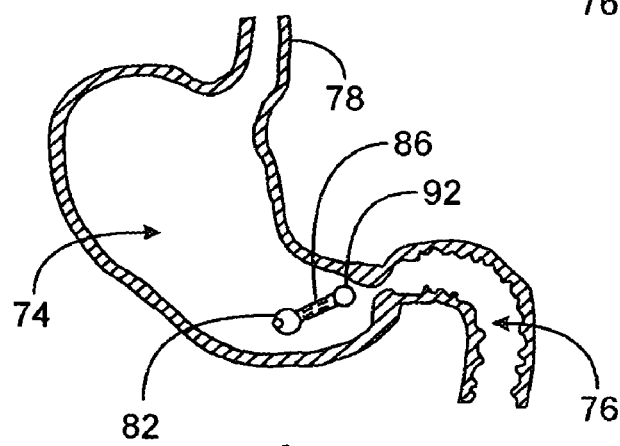
Figure 9D:
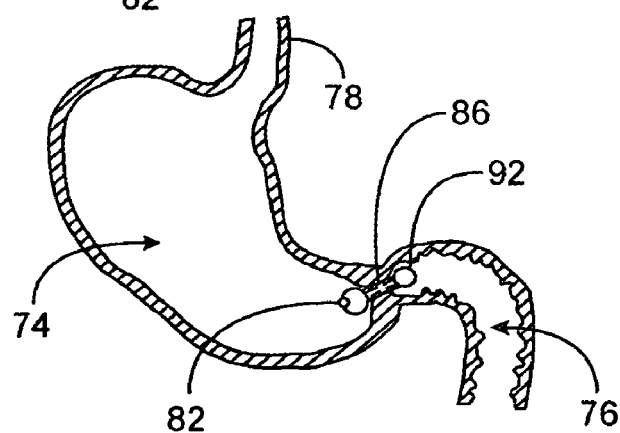

FIGS. 9A to 9D show cross-sectional views of the stomach and yet another variation for placement of a passive variation of the device 90 through ingestion. In this alternative variation, the device 90 can be ingested orally. As the device 90 enters the stomach 74, shown in FIG. 9A, both the proximal and distal occlusion members 82, 92, respectively, may be configured to inflate upon erosion of acid-sensitive coatings over the inflation port or device 90, as shown in FIGS. 9B and 9C. Once inflation or expansion has been accomplished, the distal occlusion member 92 will eventually be passed due to its smaller size (approximately the diameter of the dilated pyloric valve 5–15 mm) while the proximal occlusion member 82 will remain in the stomach 74 due to its larger size, e.g., 15 mm or greater in diameter and up to 60 mm in diameter due to physiologic limitations in the pyloric region of the stomach, as shown in FIG. 9D. Thus, one occlusion member 92 may be designed to be small enough to be passed through the pyloric valve while the proximal occlusion member 82 may be designed to be retained in the stomach 74 with both occlusion members 82, 92 inflating in the stomach 74.

Figure 10A:
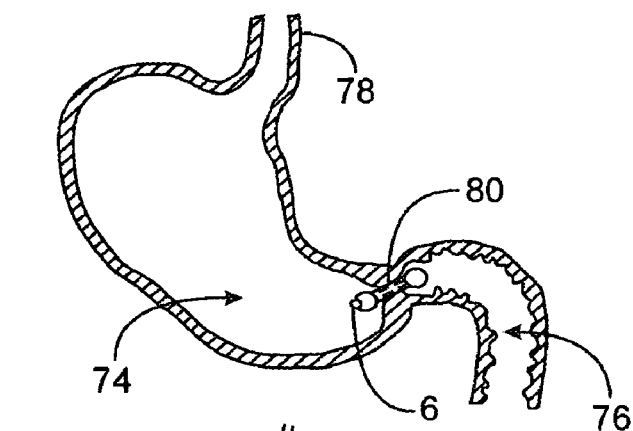
FIGS. 10A to 10D show cross-sectional views of the stomach and one variation for removal of the device.
Figure 10B:
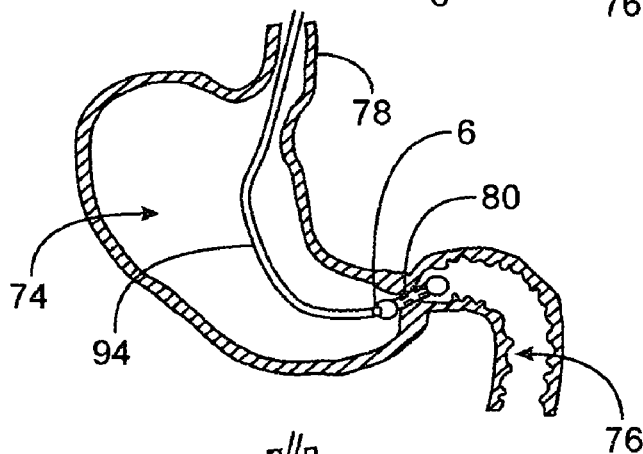
Figure 10C:
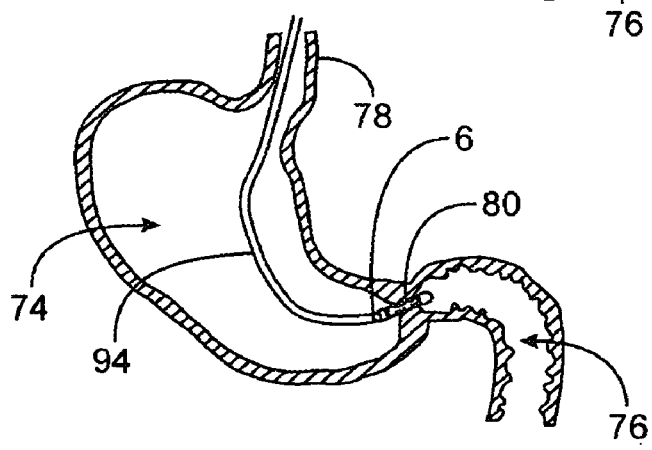
Figure 10D:
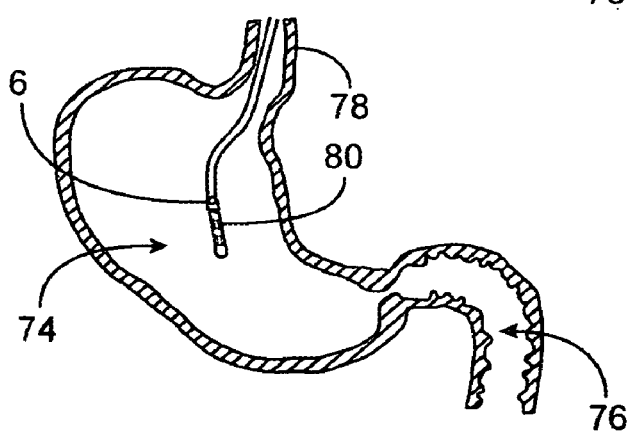

FIGS. 10A to 10D show cross-sectional views of the stomach 74 showing one variation for removal of the device 80 (passive variation illustrated). The device 80 is shown in FIG. 10A between the stomach 74 and the duodenum 76. As seen in FIG. 10B, a magnetic tipped suction catheter or endoscope 94 is introduced and the device 80 may be deflated and removed, as shown in FIGS. 10C and 10D. In contacting the inflation port 6 with the catheter 94, the tip may be configured with an electrical contact as an aid in determining whether the catheter 94 has properly contacted the inflation port 6. Alternatively, the device 80 may be removed through endoscopy or it may be designed to degrade over time and eventually be passed through the intestines.

Figure 11A:
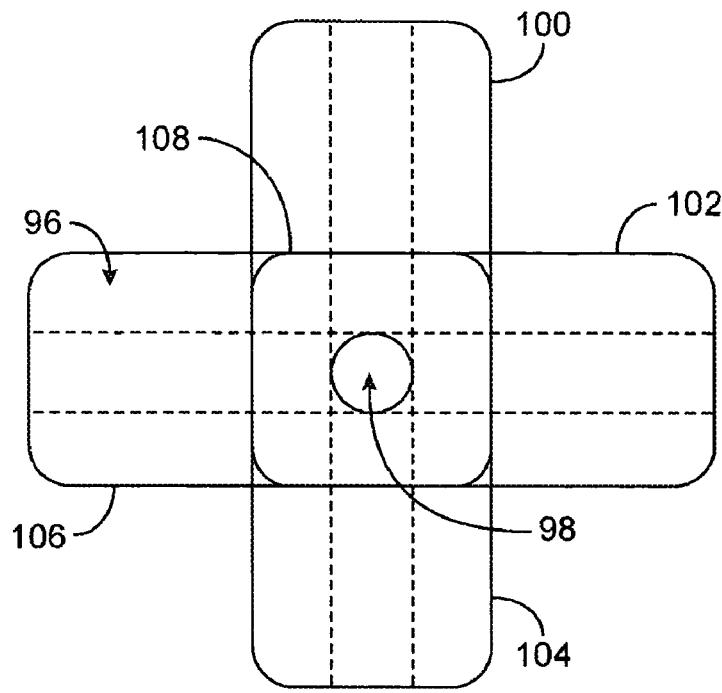
FIGS. 11A and 11B show top and perspective views, respectively, of an alternative variation of the device incorporating multiple prongs designed to intermittently obstruct the pyloric valve.
Figure 11B:
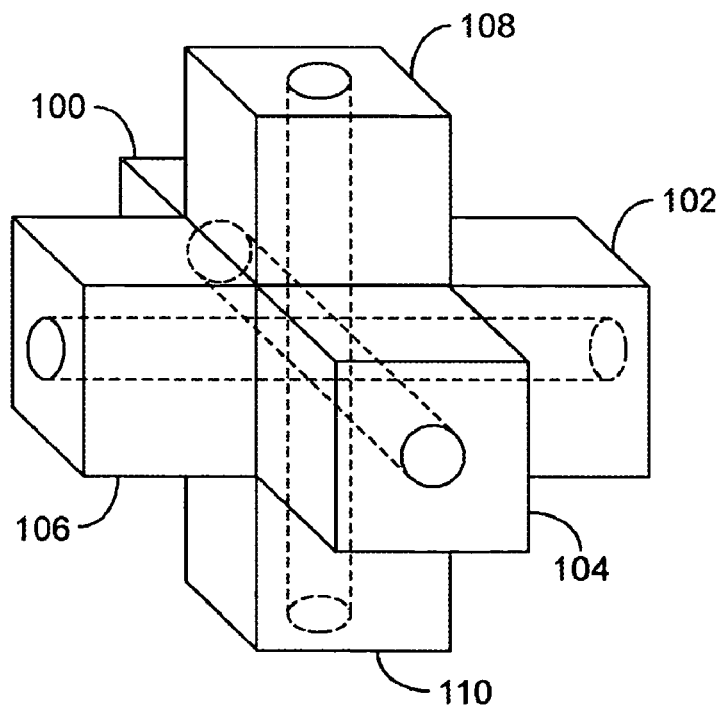

FIGS. 11A and 11B show top and perspective views, respectively, of an alternative variation for the device which may reside solely in the stomach. This particular variation may incorporate multiple prongs 100, 102, 104, 106, 108, 110 designed to intermittently cork the pylorus. In this variation, an expansile material 96 may be appropriately shaped in order to promote occlusion of the pylorus. The device may be ejected from the pylorus due to contractions, but may be re-inserted through one of the various prongs. As a further measure, the device may define multiple apertures 98 through each set of prongs to prevent complete obstruction of the pyloric valve.

Figure 12A:
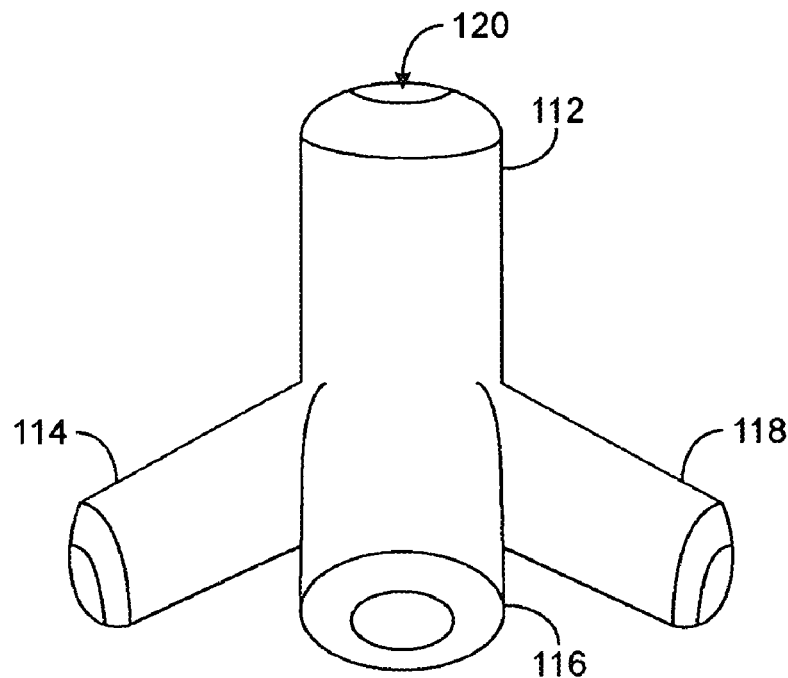
FIGS. 12A and 12B show side and top views, respectively, of another variation of the device incorporating multiple prongs designed to intermittently obstruct the pyloric valve.
Figure 12B:
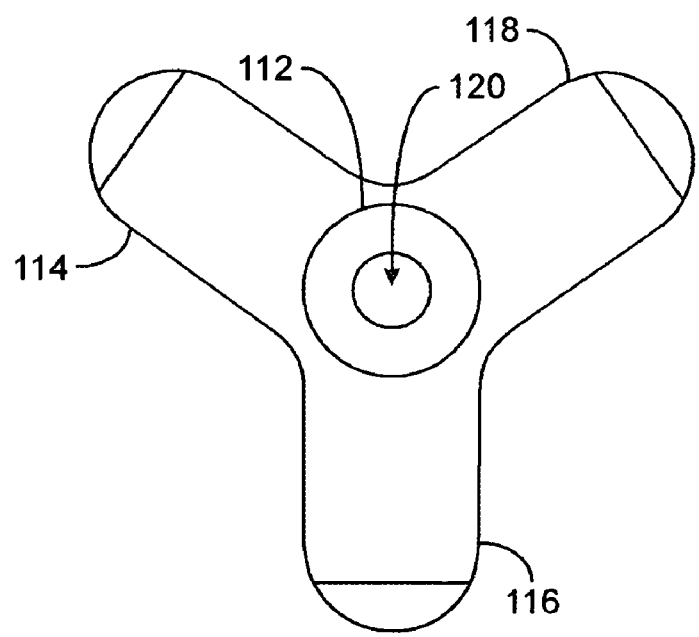
Figure 13A:
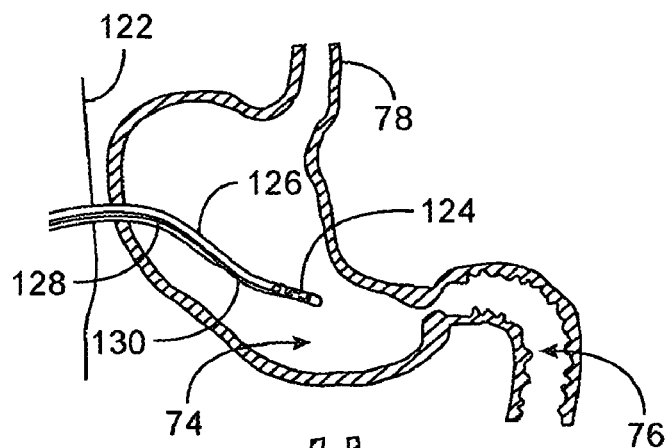
FIGS. 13A to 13D show cross-sectional views of an alternative use of the device for preventing gastroduodenal reflux during tube feeding.
Figure 13B:
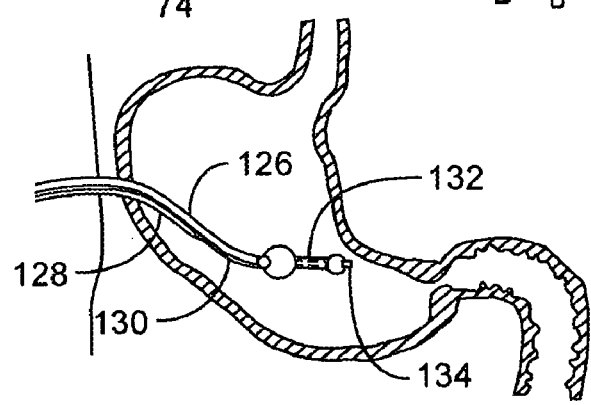
Figure 13C:
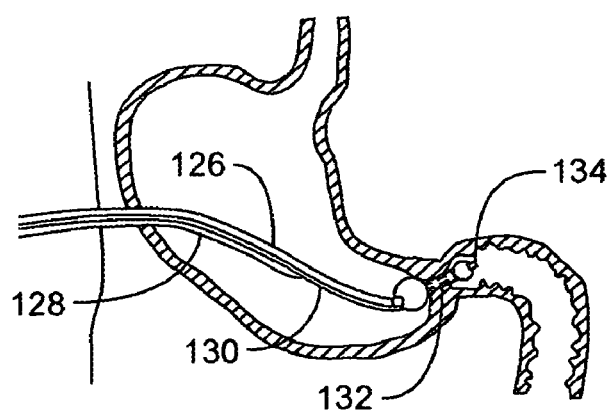
Figure 13D:
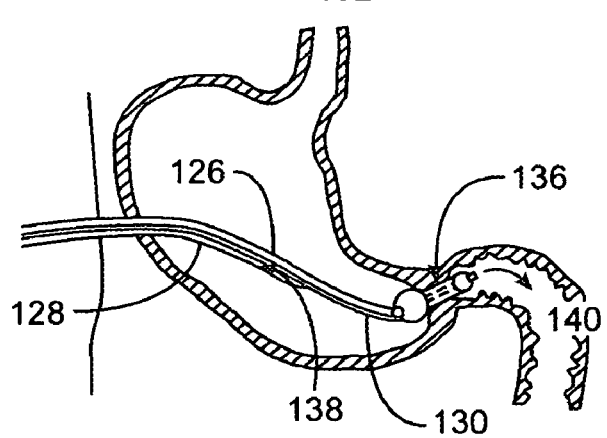

FIGS. 12A and 12B show side and top views, respectively, of another variation of the device of FIGS. 11A and 11B. In this variation, a fewer number of multiple prongs 112, 114, 116, 118 may be utilized and each prong may also define an aperture 120 therethrough. However, as shown in this variation, each of the prongs may be flexible and tapered or rounded to prevent damage to the surrounding tissue.

FIGS. 13A to 13D show cross-sectional views of an alternative use of the devices described herein. In this variation, the device may be utilized in the prevention of gastroduodenal reflux during tube feeding. As shown, the device 124 is similar to variations described above; however, in this variation, a lumen 132 defined through the device 124 for tube feed delivery may define an outlet 134 designed to be positioned in the duodenum 76. The proximal portion of the device 124 may also be attached to a feeding tube 126 and an inflation tubing 130. Feeding tube 126 may be used to deliver tube feeds through the lumen 132 directly to the duodenum 140 while the inflation tubing 130 may be used to inflate an inflatable pyloric spanner or bridging member 136 during tube feeding to prevent reflux of delivered material 140. The device 124 can also incorporate a third tube 128 which may provide for aspiration of the gastric contents 138 to prevent reflux of the delivered material into the lungs and to decompress the stomach 74. The proximal portion of the occlusive member can either maintain its inflated or expanded state or it can be decompressed at times to relieve pressure on the pyloric valve. In this variation, a percutaneous approach is shown, but a nasogastric approach or another approach is possible.

Figure 14A:
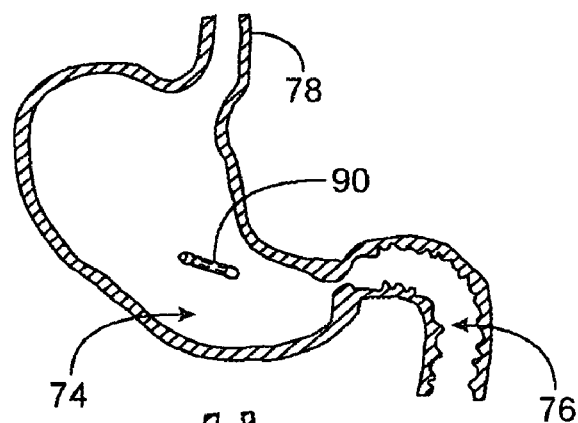
FIGS. 14A to 14D show cross-sectional views of an alternative use of the device in combination with one or several gastric fillers.
Figure 14B:
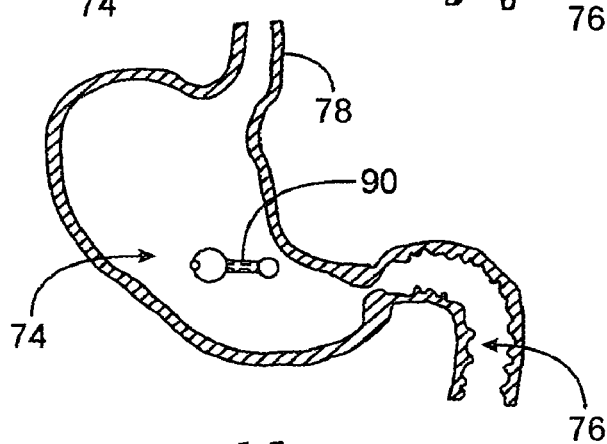
Figure 14C:
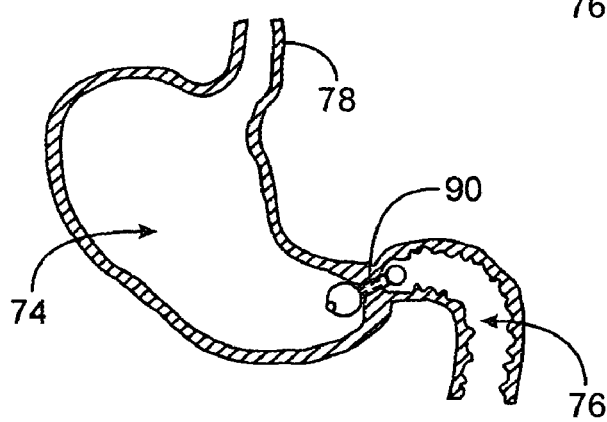
Figure 14D:
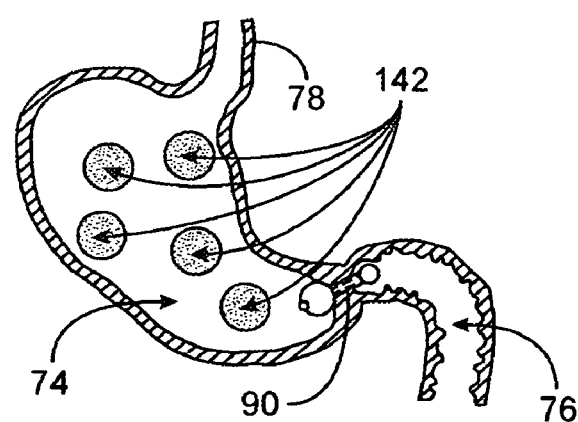

FIGS. 14A to 14D show cross-sectional views of yet another alternative use with devices of the present invention. As shown in FIGS. 14A to 14C, a device 90 may be placed to occlude the pyloric valve. In this case, the device 90 is shown as having been ingested, although placement of the device 90 may be effected via any of the methods described above. As shown in FIG. 14D, the addition of one or several gastric fillers 142, e.g., inflatable gastric balloons, expandable scaffolding, or any other number of space-occupying devices generally known in the art, may be utilized. In this variation, the device 90 may be placed and then the gastric fillers 142 may be introduced. The device 90 may be utilized to ensure that the gastric fillers 142 are not passed through the pyloric valve until they are sufficiently small, thereby allowing for non-degradable substances to be utilized without the concomitant risk of small bowel obstruction.

The applications of the inventive devices discussed above are not limited to certain treatments, but may include any number of maladies. Modification of the above-described methods and devices for carrying out the invention, and variations of aspects of the invention that are obvious to those of skill in the art are intended to be within the scope of the claims. Moreover, various combinations of aspects between examples is also contemplated and is considered to be within the scope of this disclosure.

I claim:

1. A method for intermittently obstructing a gastric opening, comprising: positioning a first occluding member proximal to the gastric opening and a second occluding member distal to the gastric opening; and
    maintaining a connection between the first occluding member and the second occluding member via a bridging member which is adapted to pass through the gastric opening such that the first occluding member obstructs the gastric opening and is retained by the second occluding member,
    wherein the bridging member is further adapted to permit the first occluding member to intermittently move relative to the gastric opening.

2. The method of claim 1 further comprising advancing the first and the second occluding members via a tubiAg member prior to positioning the first occluding member.

3. The method of claim 1 further comprising ingesting the first and the second occluding members prior to positioning the first occluding member.

4. The method of claim 3 further comprising self-expanding at least the first occluding member prior to positioning the first occluding member.

5. The method of claim 4 further comprising self-expanding the second occluding member after positioning the first occluding member.

6. The method of claim 3 further comprising self-expanding at least the first occluding member while positioning the first occluding member.

7. The method of claim 6 further comprising self-expanding the second occluding member while positioning the first occluding member.

8. The method of claim 1 further comprising expanding the first occluding member from a first configuration to a larger second configuration prior to positioning the first occluding member.

9. The method of claim 1 further comprising expanding the second occluding member from a first configuration to a larger second configuration prior to positioning the second occluding member.

10. The method of claim 1 wherein positioning the first occluding member comprises expanding the first occluding member from a first configuration to a larger second configuration.

11. The method of claim 10 wherein expanding the first occluding member comprises inflating the member with a fluid.

12. The method of claim 11 further comprising inflating the member with a visible dye or marker.

13. The method of claim 10 wherein expanding the first occluding member comprises expanding the member with an expandable foam.

14. The method of claim 10 wherein expanding the first occluding member comprises expanding the member with an expandable hydrogel.

15. The method of claim 10 wherein expanding the first occluding member comprises self-expanding the member with a shape memory alloy.

16. The method of claim 1 wherein positioning the second occluding member comprises expanding the second occluding member from a first configuration to a larger second configuration.

17. The method of claim 16 wherein expanding the second occluding member comprises inflating the member with a fluid.

18. The method of claim 17 further comprising inflating the member with a visible dye or marker.

19. The method of claim 16 wherein expanding the second occluding member comprises expanding the member with an expandable foam.

20. The method of claim 16 wherein expanding the second occluding member comprises expanding the member with an expandable hydrogel.

21. The method of claim 16 wherein expanding the second occluding member comprises self-expanding the member with a shape memory alloy.

22. The method of claim 1 wherein maintaining the connection comprises fluidly communicating between the first and the second occluding members.

23. The method of claim 1 further comprising collapsing at least the second occluding member.

24. The method of claim 23 further comprising removing the first occluding member and the second occluding member from the gastric opening.

* * * * *